(12) United States Patent
Hiltunen et al.

(10) Patent No.: US 6,365,125 B1
(45) Date of Patent: *Apr. 2, 2002

(54) PROCESS FOR THE PRODUCTION OF RADIOIODINATED NEURORECEPTOR AGENTS

(75) Inventors: Jukka Hiltunen, Helsinki; Tuomo Nikula, Numminen, both of (FI)

(73) Assignee: Map Medical Technologies OY, Tikkakoski (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/445,962

(22) PCT Filed: Jun. 15, 1998

(86) PCT No.: PCT/FI98/00514

§ 371 Date: Mar. 16, 2000

§ 102(e) Date: Mar. 16, 2000

(87) PCT Pub. No.: WO98/57909

PCT Pub. Date: Dec. 23, 1998

(30) Foreign Application Priority Data

Jun. 16, 1997 (FI) .................................................. 972550

(51) Int. Cl.$^7$ .............................................. A61K 51/00
(52) U.S. Cl. ...................................................... 424/1.85
(58) Field of Search ............................ 424/1.85, 1.81, 424/1.89

(56) References Cited

U.S. PATENT DOCUMENTS 5,310,912 A * 5/1994 Neumeyer et al. .......... 546/132
5,569,447 A   10/1996 Lee et al. ................... 424/1.85
5,976,497 A * 11/1999 Pollack et al. .............. 424/1.85

FOREIGN PATENT DOCUMENTS

| WO | 96/17630 | 6/1996 |
| WO | 96/32968 | 10/1996 |
| WO | 97/21674 | 6/1997 |
| WO | 98/18499 | 5/1998 |

OTHER PUBLICATIONS

"[123I] Iodomethane, A Main Product In The Synthesis Of 5–[123I] Iodo–6–Nitroquipazine By Iododestannylation", © 1995 by John Wiley & Sons, Ltd.

* cited by examiner

*Primary Examiner*—Michael G. Hartley
(74) *Attorney, Agent, or Firm*—Browdy and Neimark, P.L.L.C.

(57) ABSTRACT

The present invention is related to process for producing radioiodinate neuroreceptor agents with improves yields. In said process the trialkyltin group of the precursor of the neuroreceptor agent is replaced by radioiodine in the presence of an oxidation agent, preferably chloramine T in a pH adjusted by a buffering system comprising inorganic or organic acids and their salts. The end-products are subsequently separated from the by-products using chromatographic separation methods such as high performance liquid chromatography (HPLC), wherein the mobile solvent phase comprises a mixture of ethanol and water having a pH of 1–6. The improved yield are obtainable by preventing the formation of volatile radioactive by-products and by using a non-toxic solvent system in the chromatographic separation process, which simplifies the down stream processing of the end product.

14 Claims, No Drawings

PROCESS FOR THE PRODUCTION OF RADIOIODINATED NEURORECEPTOR AGENTS

CROSS REFERENCE TO RELATED APPLICATION

The present application is the national stage under 35 U.S.C. 371 of PCT/FI98/00514, filed Jun. 15, 1998.

THE TECHNICAL FIELD OF THE INVENTION

The present invention relates to a process for producing radioactively substituted neuro-receptor agents, with improved yields. The improved yields are obtainable by preventing the formation of volatile, radioactive by-products, such as methyliodine. The formation of by-products is prevented by adjusting the pH of the conversion reaction. The improved yield is also obtainable by avoiding decomposition during down stream processing. This is achievable by using a non-toxic solvent system in the separation system, which makes the subsequent evaporation, unnecessary.

THE BACKGROUND OF THE INVENTION

Neuroreceptor agents are compounds binding to specific sites in the nervous system. Because it is known that these specific binding sites are altered in some diseases or dis-orders, radiolabeled neuroreceptors are of great value for diagnosing diseases, traumas and functions of the human brain. For example, iodine-123 labeled tropane analogs have been utilized for diagnosing Parkinson's disease and dementia of the Alzheimer-type. Another group of neuroreceptor agents is substituted benzodiazepines, which are labeled with iodine-123, iodine-125 or iodine-131. For example, the density of benzodiazepine receptor complex has been reported to be altered in depression, epilepsy and panic dis-orders.

Conventionally, radioiodinated carrier-free neuroreceptor agents have been prepared by the so called Chloratnine T method using trialkyltin precursors and radioactive iodine in strongly acidic conditions. However, in some cases, the labeling reaction is associated with a large and consistent formation of a radioactive volatile reaction product: methyliodine (Y. Zea-Ponce et al., J. Lab. Comp. Rad. 1994: 36, 331–337). In said method up to 60% of the activity added into the reaction mixture is lost as by-products. The loss of such an amount of the activity is inconvenient and increases production costs, tremendously. Due to the formation of radioactive by-products, especially methyliodine, an increased amount of radioactivity has to be added into the reaction mixture, which in turn causes an increased need of radioprotection of the persons handling the early stages of the upscaling of the process. The formation of volatile, radioactive by-products, such as methyliodine, also causes the need of radioprotection in the form of devices capable of capturing volatile radiolabeled substances. Active charcoal filters, which are used to capture radioiodine from the air, do not catch up the radioactive methyliodine. Special reactor grade active charcoal filters are required and are a cause of additional production costs.

In the radioiodination method, the product has to be purified from by-products. Usually, chromatographic separation methods are used. The most preferred purification or separation method is, high performance liquid chromatography (HPLC). Conventionally, a mixture of a volatile substance, such as acetonitrile combined with water or an equivalent solvent system, has been used as an eluent. The eluent containing acetonitrile, due to its volatility, has frequently been removed by evaporation to dryness and/or mini-column recovery. However, the process of evaporation to dryness is the cause of decomposition of the labeled compounds. Up to 60% of the radiolabeled product is decomposed. This decomposition means a remarkable decrease of the total yield.

SUMMARY OF THE INVENTION

Furthermore, acetonitrile is known to be a toxic compound with tight residue limits for the injectable, radioactive products. Thus, an effective method is required to separate acetonitrile from the radiolabeled neuroreceptor agent and it is also necessary to analyze the residual acetonitrile from every single batch, which is a cause of extra costs and also delays the use of the radiolabeled neuroreceptor agent, which due to the half-life of radioactive compounds further decreases the radioactivity of the final compound.

Still, one other objective of the present invention is to provide an improved, more cost effective and more feasible method to obtain greater yields of the desired radioactive neuroreceptor agents.

Another objective of the present invention is to decrease the formation of volatile by-products such as radioactive methyliodine. At the same time another objective of the invention can be achieved, i.e. the input of radioactivity into the reaction mixture can be diminished.

Further, the objective of the invention is to avoid the use of acetonitrile in the purification and separation process and thus to avoid evaporation process for removing the acetonitrile and to further avoid the need of analysing the radiolabeled neuroreceptor agent for toxic residues.

The objectives of the present invention are achieved by using the process defined in the claims. With said new non-toxic solvent system, comprising ethanol and water in different proportions there is no need to evaporate the purified, radioactive end-product to dryness and/or to use the mini-column recovery before the final formulation and sterilization of the product. A fact that simplifies the process and reduces production costs due to decreased decomposition.

THE DETAILED DESCRIPTION OF THE INVENTION

Definitions

In the present description the terms used generally have the same meaning as in medicinal sciences including neurosciences, radiochemistry and biochemistry as set forth in text books and review articles and laboratory handbooks. Some terms are, however, used more extensively and have meaning somewhat deviating from the general use. Some of these terms are defined below.

The term radiolabeled means that the neuroreceptor agent is provided or marked with a radioactive substance or label, such as radioiodine, including I-123, etc. The term radioiodine means a radioactive isotope of iodine, such forms of iodine are e.g. iodine-123, iodine-125 and iodine-131. For diagnostic use the most preferred form of radioactive iodine is iodine-123.

The term "neuroreceptor agent" means a compound or substance characterized by its capability of specific binding to defined receptor sites or their transport receptor sites on the cells of the nervous system.

The term "improved yields" does not only encompass the direct increased yield of the end product but also encompasses the increase of yield due to the decreased formation of volatile by-products as well as the decreased decomposition of radiolabeled neuroreceptor agent in the down stream processing. The term "improved yields" also includes the need for lesser input of radioactivity to obtain a certain amount of radioactive end-product.

The term "trialkyltin group or trialkyltin precursor" means a tin-containing group, which can be used to form stable precursors of the neuroreceptor agents having the general formula (I)

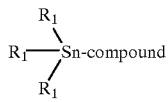

wherein the substituents $R_1$ are the same or different and mean $C_nH_{2n+1}$ groups, wherein n is 0–6 or an arylgroup. In other words the $C_nH_{2n+1}$ groups are selected from methyl, ethyl, propyl, butyl, pentyl and/or hexyl and isoforms thereof. All the alky groups in the tin compound can be the same or they can all be different. The most preferred trialkyltin groups are trimethyltin and/or tributyltin groups.

The terms "converted" and/or "conversion" mean the process wherein the trialkyltin group in the precursor of the neuroreceptor agent is replaced by or exchanged with a radioactive group, such as radioiodine.

The term "oxidation agent" means compounds or substances capable of oxidation, such compounds are for example Choramine T, peroxides, such as hydrogenperoxide, Iodogen$^R$, lactoperoxidase, succidiamides, such Promosuccidiamide, etc.

The term "chromatographic separation methods" means chromatographic methods making use of liquid-liquid phases such as high performance liquid chromatography (HPLC) and fast performance liquid chromatography (FPLC). The most preferred chromatographic separation method of the present invention is HPLC using a reversed phase column.

The term "mobile solvent phase" means the eluent used in liquid chromatography methods. The "mobile solvent phase" of the present invention is a mixture of mixture of ethanol and water (pH 1–6). The proportions of ethanol:water are preferably in the following ranges 0.5:5 to 5:0.5, most preferably 1:3 to 2:3.

The terms "adjusted pH" or "a pH adjusted with a buffering system" mean a pH range, which is not as strongly acidic as the strongly acidic conditions used in the conventional Chloramine T method. An "adjusted pH" is obtainable by using weak solutions of in-organic acids, such as HCl or using such organic acids and/or their salts known to have good buffering capacity. Preferred pH regulating systems are acetic acid/acetate, phosphoric acids/phosphate, carbonic acids/carbonates, etc.

THE GENERAL DESCRIPTION OF THE INVENTION

It was found that by using an alternative adjusted pH, which was not as strongly acidic as the pH-conditions used in the conventional Chloramine T method, the formation of radio-active volatile products could be avoided. For example the formation of radioactive methyliodine was remarkably decreased and radiohalogenated neuroreceptor agents could be produced with an increased yield.

Furthermore, a non-toxic solvent system, comprising water and ethanol was found to be effective for purifying the radioiodinated neuroreceptor agent from the trialkyltin precursor and other by-products. Said new non-toxic solvent system simplifies the process and reduces production costs. For example, there is no need of evaporating the end product to dryness and/or to use the mini-column recovery before the final formulation and sterilization.

One preferred embodiment of the present invention comprises a synthesis route, wherein the trialkyltin of neuroreceptor agent precursor is replaced by radioactive iodine. The most preferably way to carry out the production of a radioactively labeled [radioiodine] neuro-receptor agent is to replace or exchange trialkyltin with radioiodine in the presence of oxidation agent in conditions which are not strongly acidic, but have an adjusted pH. The pH used in the process of the present invention is in a range varying from a pH of at least 1 but preferably more, up to a pH of 10. Preferably the pH is in the range of 2 to 10 or preferably 8. Most preferably it is in the range of 4 to 7. The trialkyltin precursor used in the reaction is preferably a low molecular weight alkyl. Most preferably the tin precursor is trimethyltin or tributyltin.

The non-toxic solvent system of the present invention was found to purify a radioiodinated neuroreceptor compound from its trialkyltin precursor and other by-products of the reaction. With the new non-toxic solvent system, there is no need to evaporate to dryness and/or to use the mini-column recovery before the final formulation and sterilization.

To avoid radioactive volatile product, when used trialkyltin precursors, an alternative pH was found to produce radiohalogenated neuroreceptor agents. According to the present invention, formation of the radioactive methyliodine was remarkably decreased and the yield of the labeled neuroreceptor compounds increased.

The compounds, which are described on the Table 1, are used as a non-limiting example of the neuroreceptor compounds, which are synthesized from their trialkyltin precursors by the process according to the present invention.

TABLE 1

| Compound | Code Name | Structure |
| --- | --- | --- |
| [$^{123}$I]-2β-carbomethoxy-3β-(4-iodophenyl)-tropane | [$^{12}$I]-β-CIT | 1* |
| [$^{123}$I]-2β-carbomethoxy-3β-(4-iodophenyl)-nortropane | $^{123}$I]-nor-β-CIT | 2* |
| [$^{123}$I]-N-(3-fluoropropyl)-2β-carbomethoxy-3β-(4-iodophenyl)-nortropane | [$^{123}$I]-β-CIT-FP | 3* |
| [$^{123}$I]-N-(2-fluoroethyl)-2β-carbomethoxy-3β-(4-iodophenyl)-nortropane | [$^{123}$I]-β-CIT-FE | 4* |
| [$^{123}$I]-N-(3-iodo-2-propene)-2β-carbomethoxy-3β-(4-methylpenyl)-nortropane | [$^{123}$I]Pe2i | 5* |
| [$^{123}$I]-4-amino-N-[1-[3-(4-fluorophenoxy)-propyl]-4-methyl-4-piperidinyl]-5-iodo-2-methoxybenzamide | [$^{123}$I]-5-I-R91150 | 6* |
| 3-(5-cyclopropyl-1,2,4-oxadiazo-3-yl)-7-iodo-5,6-dihydro-5-methyl-6-oxo-4H-imidazo[1,5-a][1,4]-benzodiazepine | NNC 13-8241 | 7* |
| (S)-N-[1-ethyl-2-pyrrolidinyl)-methyl]-5-iodo-2,3-dimethoxybenzamide | [$^{123}$I]-Epidepride | 8* |
| 1-azabicyclo(2,2,2)oct-3-yl-α-(1-iodo-1-propen-3-yl)-α-phenylacetate | [$^{123}$I]-IQNP | 9* |

*The structures are shown on the next page

TABLE 1-continued
| Compound | Code Name | Structure |
|---|---|---|
| 1* | | 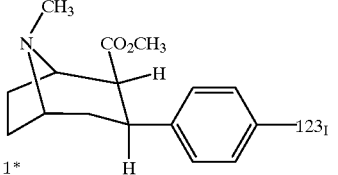 |
| 2* | | 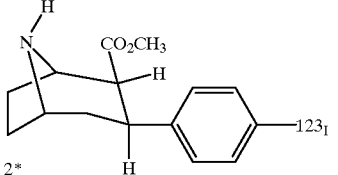 |
| 3* | | 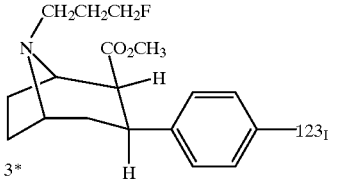 |
| 4* | | 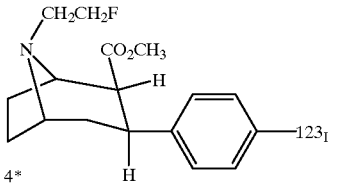 |
| 6* | | 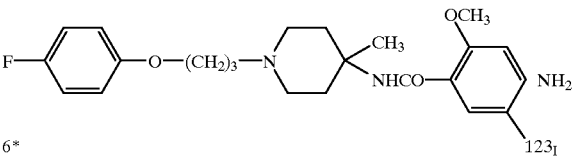 |
| 5* | | 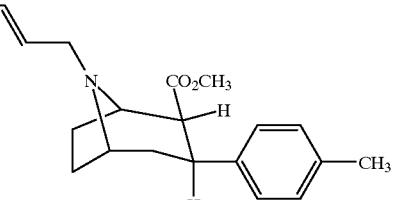 |
| 7* | | 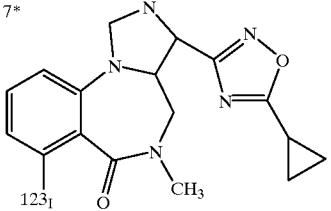 |
| 8* | | 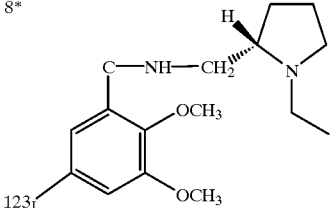 |
| 9* | | 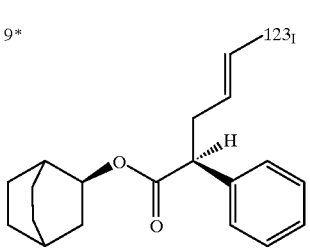 |
The main route of synthesis is outlined in flow chart 1 using Pe2i and NNC 138241 as non-limiting examples of neuroreceptor agents.
Chart 1
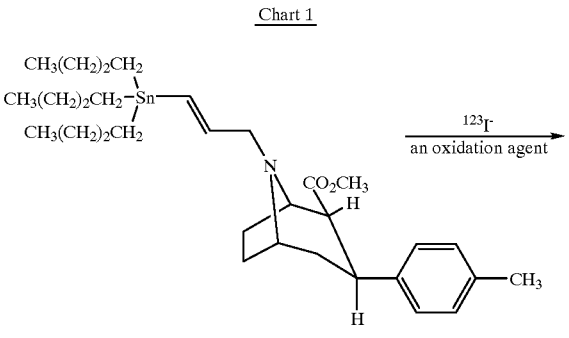
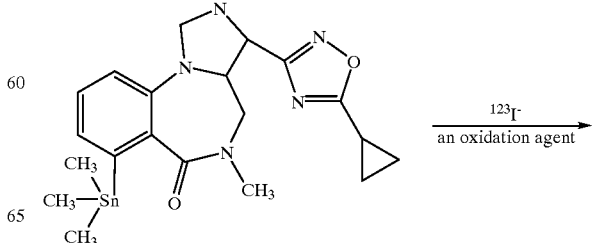

-continued

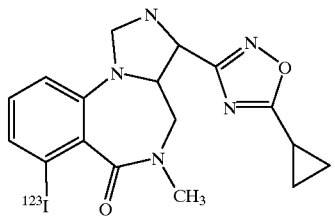

The preferred chromatographic separation method to isolate and purity the final product from precursor and other impurities is HPLC using a reversed phase column. The preferred mobile phase comprises 0.5:5 to 5:0.5 aqua (pH 1–6) and ethanol. Alternatively, the mobile phase comprises 1:3 to 2:3 aqua (pH 1–6) and ethanol. The pH is adjusted by using 0.001M to 0.1 M mineral or organic acids or their salts or by combining them.

EXPERIMENTAL

The following experiments illustrate the invention, but they are not to be constructed as limiting the invention.

EXAMPLE 1

Synthesis of [$^{125}$I] 3-(5-cyclopropyl-1,2,4-oxadiazo-3-yl)-7-iodo-5,6-dihydro-5methyl-6-oxo-4H-imidazo[1,5-a][1,4]-bernzodiazepine by iododestannylation of the precursor 3-(5-cyclopropyl-1,2,4-oxadiazo-3-yl)-7-trimethyltin-5,6-dihydro-5-methyl-6-oxo-4H-imidazo[1,5-a][1,4]-benzodiazepine 3-(5-cyclopropyl-1,2,4-oxadiazo-3-yl)-7-trimethyltin-5,6-dihydro-5-methyl-6-oxo-4H-imidazo[1,5-a][1,4]-benzodiazepine (50 μg in 50 μl ethanol), 0.1M HCl (100 μl) and Na$^{125}$I (37 MBq in 10 μl) were mixed in a small vial. Chloramine-T (50 μg in 50 μl of water) was added to the mixture which was stirred for one hour at the room temperature. The reaction mixture was injected into the HPLC μ-Bondapak-C-18 column. The mobile phase was 0.2% aqueous triethylamine (pH=7) and acetonitrile (3:5). $^{125}$I-labeled product eluted with a retention time identical to that of a non-radioactive standard reference sample. The yield after purification was 9%, with a radiochemical purity of >97%.

EXAMPLE 2

Synthesis of [$^{123}$I] 3-(5-cyclopropyl-1,2,4-oxadiazo-3-yl)-7-iodo-5,6-dihydro-5-methyl-6-oxo-4H-imidazo[1,5-a][1,4]-benzodiazepine using the Chloramine-T method A Chloramine-T solution (60 μl, 1 mg/ml) was added to a mixture of the trimethyltin precursor (50 μg in 100 μl ethanol), Na$^{123}$I solution (60 μl, 370 MBq) and 0.1M HCl (100 μl) in a 1 ml reaction vial. The reaction was allowed to proceed at room temperature for 5 min. The product [$^{123}$I] 3-(5-cyclopropyl-1,2,4-oxadiazo-3-yl)-7-iodo-5,6-dihydro-5-methyl-6-oxo-4H-imidazo[1,5-a][1,4]-benzodiazepine was separated from unreacted precursor and radioactive impurities by HPLC. The reaction mixture was injected onto the HPLC μ-Bondapak-C-18 column. The mobile phase was 0.01 M phosphoric acid and acetonitrile (60:40). The $^{123}$I-labeled product eluted with a retention time identical to that of a non-radioactive standard reference sample. After evaporation of the mobile phase the residue was redissolved in phosphate buffer and repurified with Sep-Pak mini-column. The product was eluted out of column with 3 ml ethanol and diluted with 5 ml PBS buffer, pH=7.4 and filtered through a Millipore filter (0.2 μm). The yield after purification was 10–45%, with a radiochemical purity of >98%.

EXAMPLE 3

Synthesis of [$^{123}$I] 3-(5-cyclopropyl-1,2,4-oxadiazo-3-yl)-7-iodo-5,6-dihydro-5-methyl-6-oxo-4H-imidazo[1,5-a][1,4]-benzodiazepine using the Chloramine-T method at pH 4.5

A Chloramine-T solution (100 μl, 1 mg/ml) was added to a mixture of the trimethyltin precursor (50 μg dry), Na$^{123}$I solution (100 μl, 1200 MBq) and pH was adjusted to 4.5 with 0.1% acetic acid (100 μl) in a 1 ml reaction vial. The reaction was allowed to proceed at room temperature for 5 min. The product [$^{123}$I] 3-(5-cyclopropyl-1,2,4-oxadiazo-3-yl)-7-iodo-5,6-dihydro-5-methyl-6-oxo-4H-imidazo [1,5-a][1,4]-benzodiazepine was separated from unreacted precursor and radioactive impurities by HPLC. The reaction mixture was injected onto the HPLC μ-Bondapak-C-18 column. The mobile phase was 0.01 M phosphoric acid and acetonitrile (60:40). The $^{123}$I-labeled product eluted with a retention time identical to that of a non-radioactive standard reference sample. After evaporation of the mobile phase the residue was redissolved in phosphate buffer and repurified with Sep-Pak mini-column. The product was eluted out of column with 3 ml ethanol and diluted with 5 ml PBS buffer, pH=7,4 and filtered through a Millipore filter (0.2 μm). The yield after purification was 60 to 75%, with a radiochemical purity of >98%.

EXAMPLE 4 pH versus formation of the methyliodine

Example 3 was repeated to provide labeling as mentioned above except that the pH was adjusted using suitable acetate/phosphate/carbonate buffers as indicated in Table 1 below. The reaction was allowed to proceed five to ten minutes in the sealed vial. The radioactive volatile material was removed from the reaction vial by purging with the nitrogen gas and collected into the 10 mls evacuated bottle.

TABLE 1

Effect of the reaction pH

| pH | [$^{123}$I]CH$_3$I formation % | [$^{123}$I]benzodiazepine yield % |
|---|---|---|
| 2 | 40–60 | 10 |
| 4,5 | 20–35 | 25 |
| 7,7 | 0,5 | 60 |
| 10 | 0–5 | 40 |

EXAMPLE 5 pH versus formation of the neuroreceptor compounds

Example 4 was repeated using different neuroreceptor compounds to provide labeling as mentioned above except appropriate mobile phases was used by changing 0.01 M phosphoric acid and acetonitrile ratio. The results are collected on the Table 2

TABLE 2

Yield (%) of some neuroreceptor compounds at pH 2 and 6

| Neuroreceptor precursor | pH | [$^{123}$I]CH$_3$I formation % | [$^{123}$I]-Neuroreceptor compound % |
|---|---|---|---|
| (Met)$_3$Sn-β-CIT | 2 | 5–50 | 47–95 |
| (Met)$_3$Sn-β-CIT | 6 | 0–5 | 80–95 |
| (Met)$_3$Sn-FP-β-CIT | 2 | 10–30 | 65–85 |
| (Met)$_3$Sn-FP-β-CIT | 6 | 0–5 | 80–95 |
| (Met)$_3$Sn-Epidepride | 2 | 10–50 | 40–85 |
| (Met)$_3$Sn-Epidepride | 6 | 0–5 | 80–95 |

TABLE 2-continued

Yield (%) of some neuroreceptor compounds at pH 2 and 6

| Neuroreceptor precursor | pH | [$^{123}$I]CH$_3$I formation % | [$^{123}$I]-Neuroreceptor compound % |
|---|---|---|---|
| (But)$_3$Sn-PE2i | 2 | 5–30 | 60–85 |
| (But)$_3$Sn-PE2i | 6 | 0–5 | 80–95 |

EXAMPLE 6

The yield of the neuroreceptor compound versus producing method

On the Table 3 is summarized overall yields (%) of three producing methods of the neuroreceptor compounds, where Method 1 is: A Chloramine-T solution (60 μl, 1 mg/ml) was added to a mixture of the trimethyltin precursor (50 μg in 100 μl ethanol), Na$^{123}$I solution (60 μl, 370 MBq) and 0.1M HCl (100 μl) (pH 1–2) in a 1 ml reaction vial. The reaction was allowed to proceed at room temperature for 5 min. The product was separated from unreacted precursor and radioactive impurities by HPLC. The reaction mixture was injected onto the HPLC μ-Bondapak-C-18 column. The mobile phase was appropriate mixture of 0.01 M phosphoric acid and acetonitrile (70/30 to 50/50). After evaporation of the mobile phase the residue was redissolved in phosphate buffer and repurified with Sep-Pak mini-column. The product was eluted out of column with 3 ml ethanol and diluted with 5 ml PBS buffer, pH=7.4 and filtered through a Millipore filter (0.2 μm).

Method 2: A Chloramine-T solution (60 μl, 1 mg/ml) was added to a mixture of the trimethyltin precursor (50 μg in 100 μl ethanol), Na$^{123}$I solution (60 μl, 370 MBq) and 0.1M HCl (100 μl) (pH 1–2) in a 1 ml reaction vial. The reaction was allowed to proceed at room temperature for 5 min. The product was separated from unreacted precursor and radioactive impurities by HPLC. The reaction mixture was injected onto the HPLC μ-Bondapak-C-18 column. The mobile phase was appropriate mixture of 0.01 M phosphoric acid and ethanol (70/30 to 50/50). The $^{123}$I-labeled product eluted with a retention time identical to that of a non-radioactive standard reference sample. The product was filtered through a Millipore filter (0.2 μm).

Method 3: A Chloramine-T solution (100 μl, 1 mg/ml) was added to a mixture of the trimethyltin precursor (50 μg dry), Na$^{123}$I solution (100 μl. 1200 MBq) and pH was adjusted to 6 with 0.18 M phosphate buffer (100 μl) in a 1 ml reaction vial. The reaction was allowed to proceed at room temperature for 5 min. The radiolabeled product was separated from unreacted precursor and radioactive impurities by HPLC. The reaction mixture was injected onto the HPLC μ-Bondapak-C-18 column. The mobile phase was appropriate mixture of 0.01 M phosphoric acid and ethanol (70/30 to 50/50). The $^{123}$I-labeled product eluted with a retention time identical to that of a non-radioactive standard reference sample. The product was filtered through a Millipore filter (0.2 μm).

In all cases the radiochemical purity has been over 97%.

TABLE 3

Overall yields (%) of producing method versus neuroreceptor compound

| Compound | Method 1 | Method 2 | Method 3 |
|---|---|---|---|
| [$^{123}$I]β-CIT | 70 | 85 | 95 |
| [$^{123}$I]-FE-β-CIT | 40 | 75 | 93 |
| [$^{123}$I]-FP-β-CIT | 40 | 70 | 95 |
| [$^{123}$I]-Nor-β-CIT | 55 | 85 | 93 |
| [$^{123}$I]-IQNP | 30 | 65 | 80 |
| [$^{123}$I]-Epidepride | 65 | 85 | 95 |
| NNC 13-8241 | 64 | 70 | 85 |
| [$^{123}$I]-PE2i | 65 | 80 | 93 |
| [$^{123}$I]-5-I-R91150 | 40 | 70 | 92 |

The present invention has been described above with references to specific radioiodinated neuroreceptor compounds. A person skilled in the art will know, however, that the same similar procedures may be used to provide the other radioiodinated neuroreceptor compounds of the present invention.

What is claimed is:

1. In a process for producing radioiodinated neuroreceptor compounds from a precursor compound of the formula:

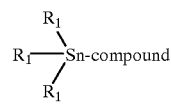

wherein the substituents $R_1$ are the same or different and are $C_nH_{2n+1}$ groups, wherein n is from 1 to 6, or an aryl group;

by replacing the trialkyl tin group of the precursor compound with a radioactive iodine group in the presence of an oxidation agent;

the improvement comprising replacing the trialkyl tin group with a radioactive iodine group in the presence of an oxidation in a pH range which is adjusted with a buffering system to be between 4 and 7 using a buffering agent selected from the group consisting of phosphoric acid, organic acids, and their salts and mixtures thereof.

2. The process according to claim 1 wherein the radioiodinated neuroreceptor compounds are separated from by-products using chromatographic separation using a mobile solvent phase comprising a mixture of ethanol and water having a pH of from 1 to 6.

3. The process according to claim 1 wherein the oxidizing agent is chloramine T.

4. The process according to claim 1 wherein the chromatographic separation method is HPLC or FPLC.

5. The process according to claim 4 wherein the chromatographic separation method is HPLC.

6. The process according to claim 5 wherein the chromatographic separation process is HPLC combined with a reverse phase column.

7. The process according to claim 2 wherein the mobile solvent phase comprises a mixture of ethanol and water in a proportion range between 0.5:5 and 5:0.5.

8. The process according to claim 7 wherein the proportion range is between 1:3 and 2:3.

9. The process according to claim 1 wherein the radioactive iodine is iodine-123.

10. The process according to claim 1 wherein the pH of the mobile phase is adjusted using as a buffering system weak solutions of inorganic acids or organic acids and their salts or by combining the acids and their salts.

11. The process according to claim 10 wherein the buffering system adjusting the pH is selected from the group consisting of acetic acid, phosphoric acids, and carbonic acids and their salts.

12. The process according to claim 11 wherein the buffering system adjusting the pH is acetic acid or its salts.

13. The process according to claim 11 wherein the buffering system adjusting the pH is phosphoric acid or its salts.

14. The process according to claim 11 wherein the buffering system adjusting the pH is carbonic acid or its salts.

* * * * *